United States Patent [19]

Johnson, Jr.

[11] 4,438,281

[45] Mar. 20, 1984

[54] SELECTIVE PRODUCTION OF MONOALKANOLAMINES FROM ALKYLENE OXIDES AND AMMONIA OVER ACIDIC INORGANIC CATALYSTS

[75] Inventor: Fred L. Johnson, Jr., Austin, Tex.

[73] Assignee: Texaco Inc., White Plains, N.Y.

[21] Appl. No.: 460,505

[22] Filed: Jan. 24, 1983

[51] Int. Cl.³ .............................................. C07C 85/18
[52] U.S. Cl. ..................................... 564/477; 564/475
[58] Field of Search ................................. 564/475, 477

[56] References Cited

U.S. PATENT DOCUMENTS 3,697,598 10/1972 Weibull et al. ...................... 564/477

OTHER PUBLICATIONS

Chemical Abstracts, vol. 77, paragraph 5243f covering Sile, M., et al., *Latv. PSR Zinat. Akad. Vestis, Kim. Ser.*, 1972,(1), pp. 54–60.

Chemical Abstracts, vol. 77, paragraph 88175j covering Sile, M., et al., *Latv. PSR Zinat. Akad. Vestis, Kim. Ser.*, 1972,(2), pp. 218–223.

*Primary Examiner*—Paul F. Shaver
*Attorney, Agent, or Firm*—Jack H. Park; Kenneth R. Priem; David L. Mossman

[57] ABSTRACT

The selective production of monoalkanolamines from alkylene oxides and ammonia over acidic inorganic catalysts such as acidic silica-aluminas, natural zeolites, acid clays and others is described. These catalysts have the advantage of providing good selectivity to the monoalkanolamine together with high alkylene oxide conversion and anhydrous operation which lowers operating costs. The catalysts are also relatively low cost and have high relative heat stability.

8 Claims, No Drawings

SELECTIVE PRODUCTION OF MONOALKANOLAMINES FROM ALKYLENE OXIDES AND AMMONIA OVER ACIDIC INORGANIC CATALYSTS

BACKGROUND OF THE INVENTION

1. Field of the Invention

The invention relates to processes for the manufacture of monoalkanolamines and more particularly relates to the anhydrous production of monoalkanolamines over acidic, inorganic catalysts.

2. Description of Other Relevant Methods in the Field

Efforts in the production of monoalkanolamines have been primarily concerned with the manufacture of monoethanolamine (MEA) from the reaction of ammonia with ethylene oxide (EO). As early as 1897 it was demonstrated by Knorr that a small proportion of water is essential to this reaction since pure ethylene oxide does not react with anhydrous ammonia (Bev., 1897, vol. 30, p. 909 and 1899, vol. 32, p. 729). For a general background on this reaction, which shows a general acceptance that it should be run in the presence of water, see Ellis, Carleton, *The Chemistry of Petroleum Derivatives*, New York: Reinhold, Vol. 1, pp. 541-544 (1934) and Vol. 2, pp. 563, 567 (1937) and Miller, S. A., *Ethylene and Its Industrial Derivatives*, London: Ernest Benn Limited, pp. 16-17, 22, 632-635 (1969). The Kirk-Othmer Encyclopedia of Chemical Technology, Third Edition describes the standard manufacture of MEA from the reaction of ethylene oxide with an excess of aqueous ammonia at a temperature of about 50° to 100° C., see vol. 1, pp. 950-952 and vol. 9, p. 437.

Alkanolamines or cycloalkanolamines are produced from epoxyalkanes or epoxycycloalkanes which are reacted with ammonia and primary or secondary amines in the presence of heat, water and inert substances with large surface areas, according to Netherlands App. 6804616 [see Derwent Abstract, Vol. 5, No. 41, Gp 5,2 (1968)].

A number of schemes have been developed which use an acid as a catalyst or co-catalyst. U.S. Pat. No. 2,186,392 reveals that ethanolamines may be produced from ammonia or a primary amine and ethylene oxide and a salt of a weak acid, such as ammonium carbonate, in the presence of an aliphatic radical which is positive with respect to hydrogen, see Chemical Abstracts (CA) 36:4131-2. Tertiary amines with hydroxyalkyl radicals may be made from ammonia, primary or secondary amines and an alkylene oxide at a temperature from 30° to 60° C., with improved yields being possible if water or a weak acid is also present, see German Pat. No. 844,449 (CA 48:1429c). British Pat. No. 497,093 teaches that monoalkylolamines may be made from olefin oxides and ammonia in the presence of water and an acid (see CA 36:4131-8).

Aluminum oxide has also been tried as a catalyst. M. Sile, et al. in a series of two articles titled "Catalyst Reaction of Ethylene Oxide with Ammonia", found that ethylene oxide and ammonia may be reacted together at high temperatures (350°-700° C.) over aluminum oxide, phosphate catalysts and 13X zeolites to yield a large number of products of which ethanolamines were only a small part, including pyridine, alpha- and gamma-picolines, acetic acid, piperazine, aziridine, diethylamine, ethylenediamine and dioxane, see Latv. PSR Zinat. Akad. Vestis, Kim. Ser., Vol. 1972, parts 1 and 2, pp. 54-60 and 218-23, respectively, (CA 77:5243f and 88175j). More specifically, aluminum oxide at 350° to 450° gives pyridine, alpha- and gamma-picolines, acetic acid, alpha-aminoethanol and dioxane; zeolite 13X at 388° to 450° gave instead pyridine, alpha- and gamma-picolines, dioxane, piperazine and a little ethylenimine, diethylamine and ethylenediamine while different phosphates gave pyridine, alpha- and gamma-picolines, acetic acid, alpha-aminoethanol and ethylenimine. Similarly, M. S. Malinovskii in J. Applied Chem. (USSR), Vol. 20, pp. 630-634 (1947) teach ethylene oxide and ammonia may be reacted together over aluminum oxide at 300° to 350° C. to produce ethanolamines and an aldehyde (CA 42:1563c).

Even some anhydrous methods have been devised. U.S. Pat. No. 3,697,598 reveals that monoalkanolamines may be made from excess ammonia and alkylene oxides without water in the presence of a cationic ion exchange resin at a temperature of at least 80° to 150° C. This U.S. patent contains a description of Swedish Pat. No. 158,167 (to the same inventor) which concerns a reaction of alkylene oxides and ammonia in an anhydrous reaction system using as a catalyst organic and inorganic acids, ammonium salts and ion exchange resins. Anhydrous systems are desirable because the water removal step is eliminated. However, ion exchange resin catalysts are not as stable in high temperature situations as is desired. A high selectivity to the monoalkanolamine as opposed to the di- and trialkanolamine is also preferred. There is a need for a process having all of these advantages and none of the disadvantages.

SUMMARY OF THE INVENTION

The invention concerns an anhydrous process for preparing monoalkanolamines which comprises reacting an alkylene oxide with an excess of ammonia in the presence of an acidic inorganic catalyst selected from the group of catalysts consisting of silica-alumina, zeolites, molecular sieves and acid clays.

DETAILED DESCRIPTION OF THE PREFERRED EMBODIMENTS

A process is provided for selectively producing monoalkanolamines from ammonia and alkylene oxides which is anhydrous and which uses inorganic acid materials as catalysts. The process is very economical to operate because almost all of the alkylene oxide is reacted, no water need be removed, the catalyst life is long and the excess ammonia may be recycled. The particular catalysts enable these various process characteristics to co-exist. The catalysts are relatively low cost and may be represented by such materials as acidic silica-aluminas, natural zeolites, acid clays, etc.

The anhydrous operation provides an energy efficient manufacturing process by eliminating the large steam requirements for water removal that are necessary in the conventional ethanolamines process. For a maximum monoalkanolamine selectivity, the reaction should be run in the liquid phase.

The process of the invention is applicable to any alkylene oxide having from two to four carbon atoms, including ethylene oxide, propylene oxide, 1,2-butylene oxide, 2,3-butylene oxide and isobutylene oxide. The major product is therefore the corresponding monoalkanolamine, such as monoethanolamine, monopropanolamine and monobutanolamine. Di- and trialkanolamines may also be produced in small yields and they may be removed if desired. However, an important advantage of the instant process is the unusually high selectivity to the monoalkanolamine.

Ammonia is, of course, an essential co-reactant, but it should be present in anhydrous form only to prevent the need to remove the water in the reactant stream.

The catalyst should be an inorganic acidic material that is heterogeneous as compared with the liquid reactants. Preferred compounds are acidic silica-aluminas, zeolites, molecular sieves, acid clays or other acid metal oxides. The especially preferred catalysts are the silica-aluminas also known as aluminosilicates. These catalysts typically contain a proportion of aluminum oxide. These catalysts give a high selectivity to the monoalkanolamine, are relatively economical and are highly heat stable. The catalysts should be in a particulate form, suitable for a fixed bed process. Beads, granules and pellets are preferred.

The reaction should be carried out under a pressure that is at least as high as the vapor pressure of ammonia at the highest temperature to which the reaction mixture is brought during the reaction to ensure that the reactants remain in the liquid phase throughout the reaction. This pressure is expected to be in the range of 500 to 2,000 psig. The preferred temperature range is from about 50° to 132° C. An especially preferred range for MEA production is from 75° to 132° C.

An excess of ammonia should be used. The molar ratio of ammonia to alkylene oxide should be in the range from about 10:1 to about 40:1. Using these mole ratios, a yield to the monoalkanolamine of 70 to 90% and higher is possible. Generally, the yield to the monoalkanolamine increases as the mole ratio of ammonia to oxide is increased with 40:1 as the upper limit beyond which additional ammonia is not beneficial.

After conclusion of the reaction, the ammonia is easily separated by reducing the pressure to below that at which the ammonia is in a gaseous phase, so that the ammonia can be separated as a gas, and then recycled. The gaseous recycled ammonia is, of course, repressurized to the liquid phase before blending with more alkylene oxide. It is also possible to distill off the unreacted ammonia under pressure and recycle it as a liquid. The pressure over the alkanolamine mixture is then released.

The alkanolamine reaction mixture is composed predominantly of monoalkanolamine, and can be used as such, if minor amounts of di- and trialkanolamines can be tolerated. If pure monoalkanolamine is desired, it can be separated from the other alkanolamines by fractional distillation. The di- and trialkanolamines can be separated from each other in the same way.

The invention may be further illustrated by the following examples which demonstrate particular embodiments of the invention.

EXAMPLE 1

The reactor consisted of a 1 inch stainless steel tube inside a jacket containing refluxing toluene for temperature control. The catalyst was W. R. Grace & Co. type 980 silica-alumina (25% $Al_2O_3$) pellets, 3/16" diameter. The catalyst volume was approximately 310 cc with a bed depth of approximately 34". Feeds were not preheated. Ammonia and ethylene oxide feeds were separately pumped to the reactor, mixing just prior to entering the catalyst bed. Anhydrous ammonia and ethylene oxide were fed to the reactor.

| Run Conditions and Results | |
|---|---|
| Reactor pressure, psig | 1450 |
| Mole ratio, $NH_3$/EO | 39.88 |
| Reactor jacket temp., °C. | 110 |
| Liquid hourly space velocity (LHSV) | 0.97 g feed/cc cat/hour |
| Length of run, hours | 3 |
| Analysis (gas chromatography, Area %, $NH_3$ free basis) | |
| Monoethanolamine | 87.04 |
| Diethanolamine | 10.12 |
| Triethanolamine | 2.10 |
| Approximate EO conversion, % | 98 |

EXAMPLE 2

The same catalyst and reactor were used as in Example 1 but a lower $NH_3$/EO mole ratio was used.

| Run Conditions and Results | |
|---|---|
| Reactor pressure, psig | 1450 |
| Mole ratio, $NH_3$/EO | 27.7 |
| Reactor jacket temp., °C. | 110 |
| Liquid hourly space velocity (LHSV) | 0.75 |
| Length of run, hours | 8.0 |
| Analysis (gas chromatography, Area %, $NH_3$ free basis) | |
| Monoethanolamine | 83.54 |
| Diethanolamine | 13.84 |
| Triethanolamine | 2.16 |
| Approximate EO conversion, % | 85 |

EXAMPLE 3

The same type of catalyst and reactor configuration were used as in Example 1 except that the mole ratio of reactants was changed.

| Run Conditions and Results | |
|---|---|
| Reactor pressure, psig | 1550 |
| Mole ratio, $NH_3$/EO | 18.22 |
| Reactor jacket temp., °C. | 110 |
| Liquid hourly space velocity (LHSV) | 2.35 |
| Length of run, hours | 6 |
| Analysis (gas chromatography, Area %, $NH_3$ free basis) | |
| Monoethanolamine | 76.11 |
| Diethanolamine | 19.42 |
| Triethanolamine | 4.39 |
| Approximate EO conversion, % | 75 |

EXAMPLE 4

The same reactor configuration was used here as in the previous examples. The catalyst used was LINDE ® Type AW-500 molecular sieves, in a quantity of about 375 cc.

| Run Conditions and Results | |
|---|---|
| Reactor pressure, psig | 1550 |
| Mole ratio, $NH_3$/EO | 16.72 |
| Reactor jacket temp., °C. | 110 |
| Liquid hourly space velocity (LHSV) | 1.69 |
| Length of run, hours | 5 |
| Analysis (gas chromatography, Area %, $NH_3$ free basis) | |
| Monoethanolamine | 81.42 |

| Run Conditions and Results | |
|---|---|
| Diethanolamine | 16.51 |
| Triethanolamine | 2.01 |
| Approximate EO conversion, % | 82 |

EXAMPLE 5

The same reactor configuration and catalyst were used as in Example 4. The jacket temperature was changed to 125° C. instead of 110° C.

| Run Conditions and Results | |
|---|---|
| Reactor pressure, psig | 1550 |
| Mole ratio, NH$_3$EO | 17.65 |
| Reactor jacket temp., °C. | 125 |
| Liquid hourly space velocity (LHSV) | 1.79 |
| Length of run, hours | 3 |
| Analysis (gas chromatography, Area %, NH$_3$ free basis) | |
| Monoethanolamine | 74.68 |
| Diethanolamine | 22.01 |
| Triethanolamine | 3.27 |
| Approximate EO conversion, % | 98 |

EXAMPLE 6

This was a comparative run which used the same reactor configuration and feed system as the previous runs but 3 mm PYREX ® glass beads were loaded into the reactor instead of catalyst. The beads served as a heat transfer material.

| Run Conditions and Results | |
|---|---|
| Reactor pressure, psig | 1550 |
| Mole ratio, NH$_3$/EO | 15.70 |
| Reactor jacket temp., °C. | 125 |
| Liquid hourly space velocity (LHSV) | 1.88 |
| Length of run, hours | 5 |
| Analysis (gas chromarography, Area %, NH$_3$ free basis) | |
| Monoethanolamine | 83.67 |
| Diethanolamine | 13.06 |
| Triethanolamine | 3.27 |
| Approximate EO conversion, % | 22 |

Although selectivity to MEA was good, conversion of EO was very poor.

Many modifications may be made in the process of this invention without departing from the spirit and scope of the invention which is defined only by the appended claims. For example, one skilled in the art could optimize the yield and selectivity to the monoalkanolamine by altering the temperature, pressure, reactant ratio or mode of addition from those explicitly shown here.

I claim:

1. An anhydrous process for preparing monoalkanolamines which comprises reacting an alkylene oxide with an excess of ammonia in the presence of an acidic inorganic catalyst selected from the group of catalysts consisting of silica-alumina, zeolites, molecular sieves and acid clays.

2. The process of claim 1 in which the monoalkanolamines and the alkylene oxides have from two to four carbon atoms.

3. The process of claim 2 in which the monoalkanol amine is monoethanolamine and the alkylene oxide is ethylene oxide.

4. The process of claim 1 in which the process is conducted continuously and in the liquid phase.

5. The process of claim 1 in which the molar ratio of ammonia to alkylene oxide is within the range of from about 10:1 to about 40:1.

6. The process of claim 1 in which the pressure ranges from about 500 to 2,000 psig and the temperature ranges from about 50° to 132° C.

7. The process of claim 1 in which the catalyst contains a metal oxide.

8. A continuous anhydrous process for preparing monoethanolamine which comprises continuously reacting ethylene oxide with ammonia in the liquid phase, in a molar ratio of ammonia:ethylene oxide within the range from about 10:1 to about 40:1, at a pressure from about 500 to about 2,000 psig and at a temperature within the range from about 75° to 132° C. in the presence of a silica-alumina catalyst, to give a yield to monoethanolamine between 70 and 90%.

* * * * *